United States Patent [19]

Kishii et al.

[11] Patent Number: 5,153,099
[45] Date of Patent: Oct. 6, 1992

[54] WAVELENGTH MULTIPLEXED OPTICAL RECORDING MATERIAL

[75] Inventors: Noriyuki Kishii; Shinichiro Tamura; Nobutoshi Asai; Koichi Kawasumi; Junetsu Seto, all of Kanagawa, Japan

[73] Assignee: Director General, Agency of Industrial Science and Technology, Tokyo, Japan

[21] Appl. No.: 500,239

[22] Filed: Mar. 26, 1990

Related U.S. Application Data

[63] Continuation of Ser. No. 199,266, May 26, 1988, abandoned.

[30] Foreign Application Priority Data

May 27, 1987 [JP] Japan .................. 62-128350
May 27, 1987 [JP] Japan .................. 62-128351

[51] Int. Cl.⁵ .............................. G03C 1/73
[52] U.S. Cl. .................. 430/270; 430/495; 430/945; 346/135.1; 540/145
[58] Field of Search ........ 430/495, 945, 270; 346/135.1; 540/145

[56] References Cited

U.S. PATENT DOCUMENTS 2,950,237  8/1960  Sharp ..................... 540/145
4,101,976  7/1978  Castro et al. ............ 365/119
4,533,211  8/1985  Bjorklund et al. ......... 350/162.12

FOREIGN PATENT DOCUMENTS 61981  3/1987  Japan .

OTHER PUBLICATIONS

Chemical Abstracts 106:83842g.
Chemical Abstracts 104:76017x.
J. Het. Chem., vol. 3, No. 4, pp. 495-502, Gupta et al., "Synthetic Porphyrins".

Primary Examiner—Charles L. Bowers, Jr.
Assistant Examiner—Thorl Chea
Attorney, Agent, or Firm—Hill, Van Santen, Steadman & Simpson

[57] ABSTRACT

A wavelength multiplexed optical recording material is disclosed wherein a photosensitive material including substituted porphine, such as tetra(pentafluorophenyl) porphine or tetra(4-methoxyphenyl) porphine, is uniformly dispersed into an optically transparent dispersion medium. When such wavelength multiplexed optical recording material is cooled to a temperature of liquid helium and irradiated with a laser beam, a large number of holes of narrow width are formed in an inhomogenous absorption band under the phenomenon of photochemical hole burning. As compared to unsubstituted porphine, the above porphine derivatives give an improved recording sensitivity and narrow hole width.

2 Claims, 5 Drawing Sheets

WAVELENGTH MULTIPLEXED OPTICAL RECORDING MATERIAL

This is a continuation of application Ser. No. 199,266, filed May 26, 1988, now abandoned.

BACKGROUND OF THE INVENTION

1. Field of the Invention

This invention relates to a wavelength multiplexed optical recording material permitting high density recording through the utilization of the phenomenon of photochemical hole burning.

2. Description of the Prior Art

At present, the optical disk has become most popular as the high density optical recording medium. Recording on the disk is performed by irradiating the disk with a recording laser beam which is narrowed to a diameter of the order of several microns, and the information is recorded in the form of changes in the optical concentration on the recording medium or in the form of changes in profile such as pit formation on the recording medium. Hence, only the information corresponding to one bit can be recorded at each laser spot, so that a limitation is imposed on increasing the recording density.

To overcome the limitation on the recording density, the concept of the so-called wavelength multiplexed recording has recently been introduced, according to which plural information units are recorded in each spot upon changing the wavelength of the recording laser. As one such system for wavelength multiplexed optical recording, a system employing a recording composition containing plural substances exhibiting photosensitivity to plural wavelengths has been reported for example in the Electronic Communication Association Technological Research Reports (CPM 82-55, pages 9 to 16). With this known system, the number of the information units that can be recorded in one spot is not larger than ten.

As a wavelength multiplexed optical recording system, separate from the above system, there is also known a method resorting to photochemical hole burning, the recording principle of which is described for example in the Japanese Laid-Open Patent Publication No. 53-99735 corresponding to the U.S. Pat. No. 4101976. According to this method, a broader absorption band the photosensitive material dispersed into the transparent medium exhibits at an ultra low temperature, hereafter referred to as the inhomogeneous absorption band, is irradiated with a laser beam of narrow bandwidth for forming sharply defined recesses, hereafter referred to as holes, in the absorption band. A large number of such holes can be formed in the inhomogeneous absorption band by changing the wavelength of the laser beam at small variations. Theoretically, it should be possible to form $10^2$ to $10^3$ holes in each inhomogeneous absorption band. This system is thought to be promising for high density recording since the number of the information units in each spot can be drastically increased through the utilization of the presence or absence of these holes for bit recording.

The photosensitive materials so far known to exhibit photochemical hole burning include porphine, chlorin, phthalocyanin, quinizarin or tetrazin, in addition to chromoproteins such as chlorophyle or phycocyanin.

It is noted that, in a photochemical reaction in general, the ratio of the number of the reacted molecules to that of the photons absorbed in the reaction system, that is, the so-called quantum yield, has been recognized as a critical factor. The material excellent in the quantum yield is advantageously employed for improving the recording sensitivity. This means that, when the light source of a predetermined light intensity is employed, the same effect may be achieved by the irradiation continuing for a shorter time interval, so that a high-speed recording may be achieved. However, it is thought that the photoisomerization reaction in the photochemical hole burning proceeds in many cases through the excited triplet state, this process being the rate-determining step. Therefore, it has been difficult to achieve a high speed in a number of materials thus far studied as the photosensitive material, so that it has not been possible to achieve satisfactory recording sensitivity.

On the other hand, the degree of multiplexing in photochemical hole burning is determined by the number of independent holes having a hole width $\Delta w_h$ that can be formed in an inhomogeneous absorption band having a band width $\Delta w_i$. Usually, the value of the ratio $\Delta w_i/2\Delta w_h$ is adopted as the measure of the degree of multiplexing. However, with the aforementioned known compounds, the multiplexing degree cannot be increased beyond a certain limit value because only larger hole widths can be attained with these compounds. In addition, in the known compounds, side holes may be produced to deteriorate the recording signals, while the saturation of the recording signals occurs at an earlier stage such that the S/N ratio cannot be elevated satisfactorily. Thus the known compounds cannot be employed for practical usage or application.

SUMMARY OF THE INVENTION

It is an object to provide an optical recording system employing the photochemical hole burning, wherein porphine derivatives are employed as the photosensitive material to narrow the hole width to improve the recording density while simultaneously improving the recording intensity without producing side holes for achieving the recording with an improved S/N ratio.

It is another object of the present invention to provide such system wherein the wavelength multiplexed recording material has an improved sensitivity to achieve high speed recording indispensable for high density recording.

In the present specification, the hole width means the half value width.

When an absorption spectrum is measured of a porphine derivative uniformly dissolved in a diluted state in a transparent dispersion medium and cooled to an ultralow temperature, a microscopic difference is induced in the energy state of the individual molecules due to the interaction with the material of the dispersion medium, so that an absorption band exhibiting a certain broadening, that is, an inhomogeneous absorption band, will be observed. When the porphine derivative in this state is irradiated with a narrow bandwidth laser beam of a predetermined wavelength, only the molecules having the energy corresponding to this wavelength are able to absorb the laser beam, so that a hole is produced in the inhomogeneous absorption band. For increasing the number of holes produced in one inhomogeneous absorption band, there are two alternative methods, that is, increasing the width $\Delta w_i$ of the inhomogeneous absorption band, or reducing the width $\Delta w_h$ of the individual holes.

According to the present invention, by using tetra (pentafluorophenyl)porphine, obtained upon introducing fluorine atoms into the benzene ring of tetraphenylporphine, as the photosensitive material, it is possible to reduce the hole width $\Delta w_h$ as compared to tetraphenylporphine not having substituents in the benzene ring, and to increase the recording intensity without producing side holes. This is presumably ascribable to the reduced surface energy of the molecules caused by introduction of the fluorine atoms into the benzene ring and to the resulting reduction in the interaction with the ambient material of the dispersion medium.

Also, according to the present invention, by using tetra (4-methoxyphenyl)porphine, obtained upon introducing electron donative substituents, especially methoxy groups, into the benzene ring of tetraphenylporphine, recording sensitivity can be improved significantly and the S/N ratio can also be improved while it becomes possible to achieve high-speed recording. The material exhibits improved recording intensity as compared to tetraphenylporphine not having substituents in the benzene ring, this being possibly ascribable to the increased electron density on the nitrogen atom at the reaction center and to the facilitated proton movement due to introduction of the electron donative substituents.

Therefore, by using these porphine derivatives, it is possible to achieve ultra high density recording by photochemical hole burning.

DETAILED DESCRIPTION OF THE INVENTION

Figure 1:
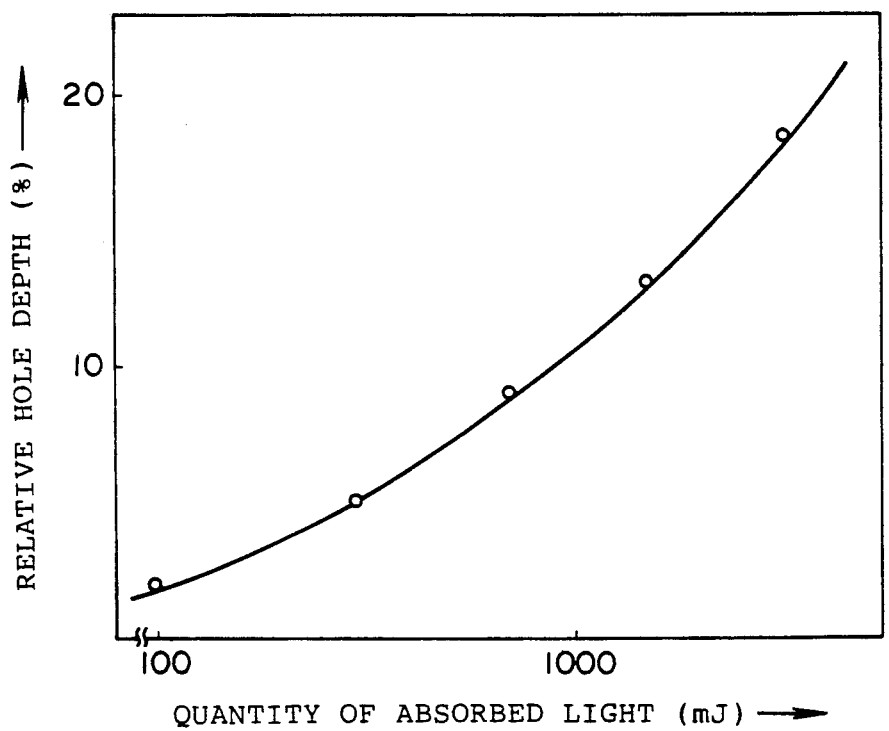
FIG. 1 is a characteristic diagram showing the relation between the relative hole depth and the absorbed light quantity in a recording obtained upon employing a wavelength multiplexed recording material containing tetra (pentafluorophenyl)porphine.

The wavelength multiplexed optical recording material according to the present invention is a uniform dispersion of a photosensitive material in an optically transparent dispersion medium, wherein the photosensitive material is tetraphenylporphine including substituents. The material is represented by the following general formula I:

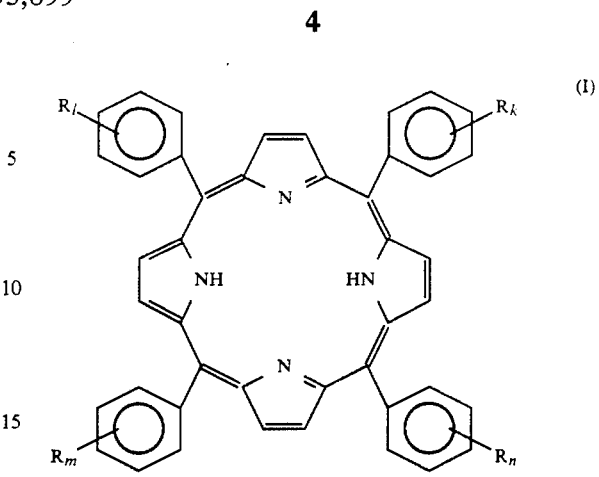

(I)

wherein R represents substituents and k, l, m and n represent integers of 1 to 5.

The substituents may be suitably selected depending on the desired properties. One possible substituent is fluorine, in which case the photosensitive material is represented by the following formula II:

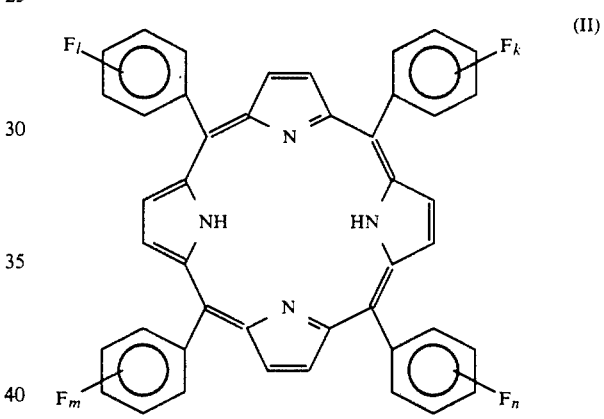

(II)

wherein k, l, m and n represent integers of from 1 to 5. It is noted that, while there is no limitation on the number of the fluorine substituents, excellent results proper to pentafluoro substituents have been specifically recognized in the present invention. In terms of recording sensitivity, electron donative substituents are favorably used, those assuming a negative value of the substituent constant $\sigma$ in accordance with the Hammett's rule may be employed. Such electron donative substituents include methoxy-, alkyl-, alkoxy- or dimethylamino groups. Above all, superior results proper to the methoxy groups have been recognized in the present invention.

If, with the use of the above materials, more and more holes are to be formed in the inhomogeneous absorption band observed at an extremely low temperature, it may be contemplated to increase the width of the inhomogeous absorption band and/or to reduce the hole width. For increasing the inhomogeneous absorption band width $\Delta w_i$, it is preferred to use an amorphous medium and, for reducing the hole width $\Delta w_h$, it is important that the structure and/or the combination of the photosensitive material and the dispersion medium be so designed that the interaction with phonon will be lowered. On the other hand, in a system exhibiting a stronger coupling between the photosensitive material and the dispersion medium, the side holes may be produced with deterioration in the S/N ratio of the recording signals. Therefore, a system with the weaker coupling is preferably employed.

The dispersion medium should be selected in view of the above requirements. Thus, an organic glass system such as an ethanol/methanol system, tetrahydrofuran or glycerol, a crystal medium containing n-alkane (Shpol'-skii matrix) or polymer resins, such as polystyrene, polyethylene, polyvinyl alcohol or polymethylmethacrylate, may be employed. However, any other dispersion media may be employed on the condition that they do not exhibit absorption in the electron absorbing region of the photosensitive material employed while being able to disperse the photosensitive material uniformly and free from cracking at an extremely low temperature.

In recording, a specimen consisting of the aforementioned photosensitive material added in an amount of about $1 \times 10^{-4}$ percent to a suitable dispersion medium is prepared. This concentration is an approximate value necessary to realize the dilute state and can be suitably selected as a function of the kinds of the photosensitive material and the dispersion medium employed. The sample is cooled to an extra low temperature and irradiated with a laser light having a wavelength suited to the photosensitive material.

The present invention will be further explained by referring to several examples.

EXAMPLE 1

A sample consisting of tetra(pentafluorophenyl)porphine having the general formula III:

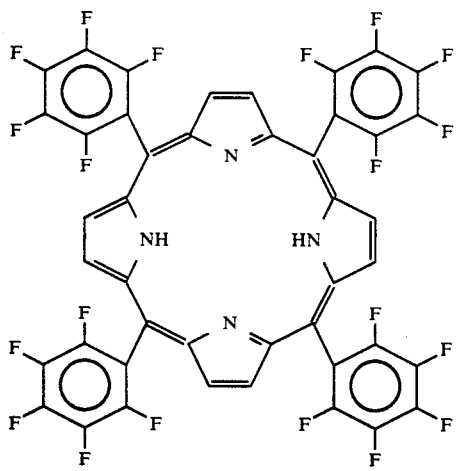

added in on amount of $1.2 \times 10^{-4}$ percent by weight to polymethylmethacrylate was prepared. After the sample was cooled to 4K, recording was made employing a dye laser having an oscillation wave number of 15320.9 cm$^{-1}$ (wavelength, 6527Å) and an oscillation energy of 0.2 mW/cm$^2$ and changes in the relative hole depth caused by the changes in the absorbed light quantity were checked. The relative hole depth herein means the rate in percentage of the decrease in absorbancy caused by hole formation to the absorbancy prior to the occurrence of the photochemical hole burning, and may be used as a measure of the recording intensity. The results are shown in FIG. 1 wherein the ordinate denotes the relative hole depth and the abscissa the absorbed light quantity expressed in a logarithmic scale. It is seen from this figure that complete recording saturation is not reached within the range of observation for the present experiment, and that the recording intensity of the order of 18 percent may be achieved in terms of the relative hole depth.

Figure 2:
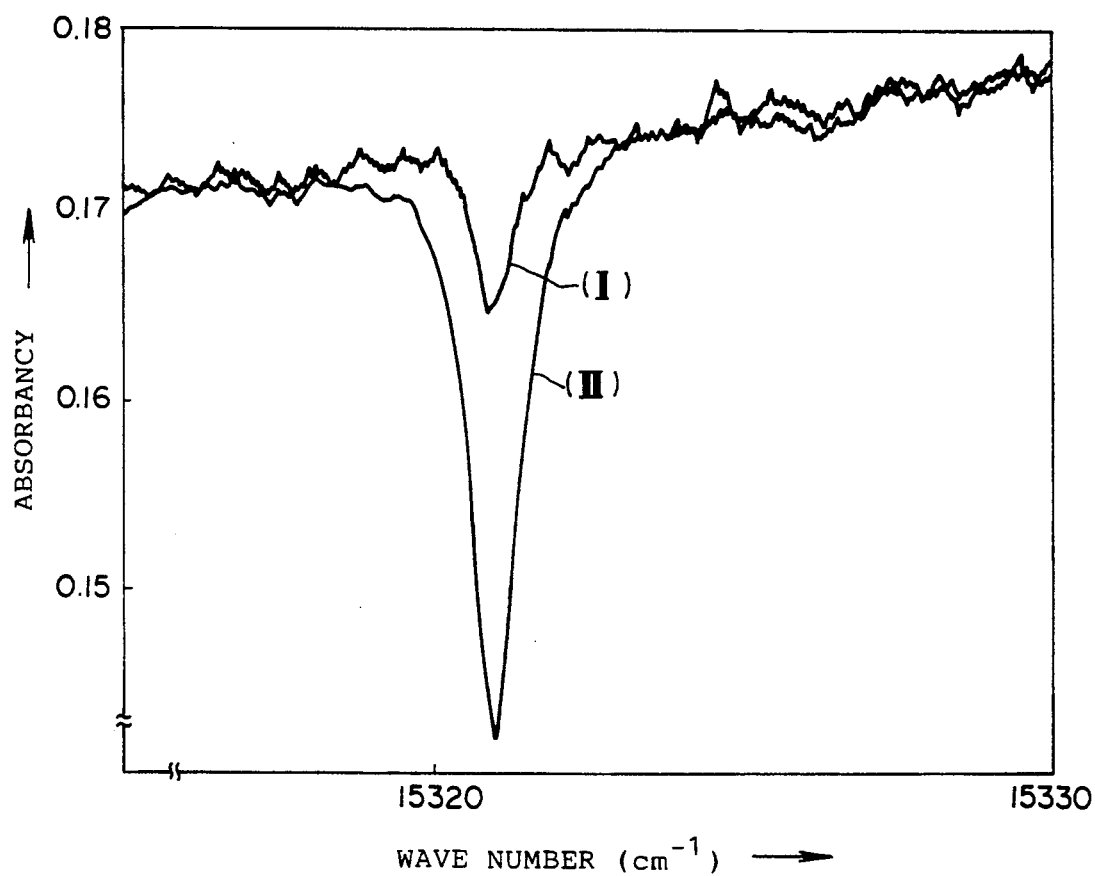
FIG. 2 shows a spectrum for the recording state obtained upon employing a wavelength multiplexed recording material containing tetra(pentafluorophenyl)-porphine.

FIG. 2 shows the spectrum of the recording state which was obtained under the irradiation condition of the laser light beam capable of achieving the recording strengths of 5 and 18 percents. In the figure, the ordinate and the abscissa represent absorbancy and the number of oscillation waves, respectively, and the curves I and II represent the spectra at the recording intensities of 5 and 18 percents, respectively. It is seen from the figure that the hole width is not increased when the recording intensity is increased from 5 to 18 percent so that it is possible to achieve the recording that is high in recording intensity and highly multiplexed in the wavelength domain. It is also possible to achieve recording with a superior S/N ratio since side holes are not produced.

COMPARATIVE EXAMPLE

Figure 3:
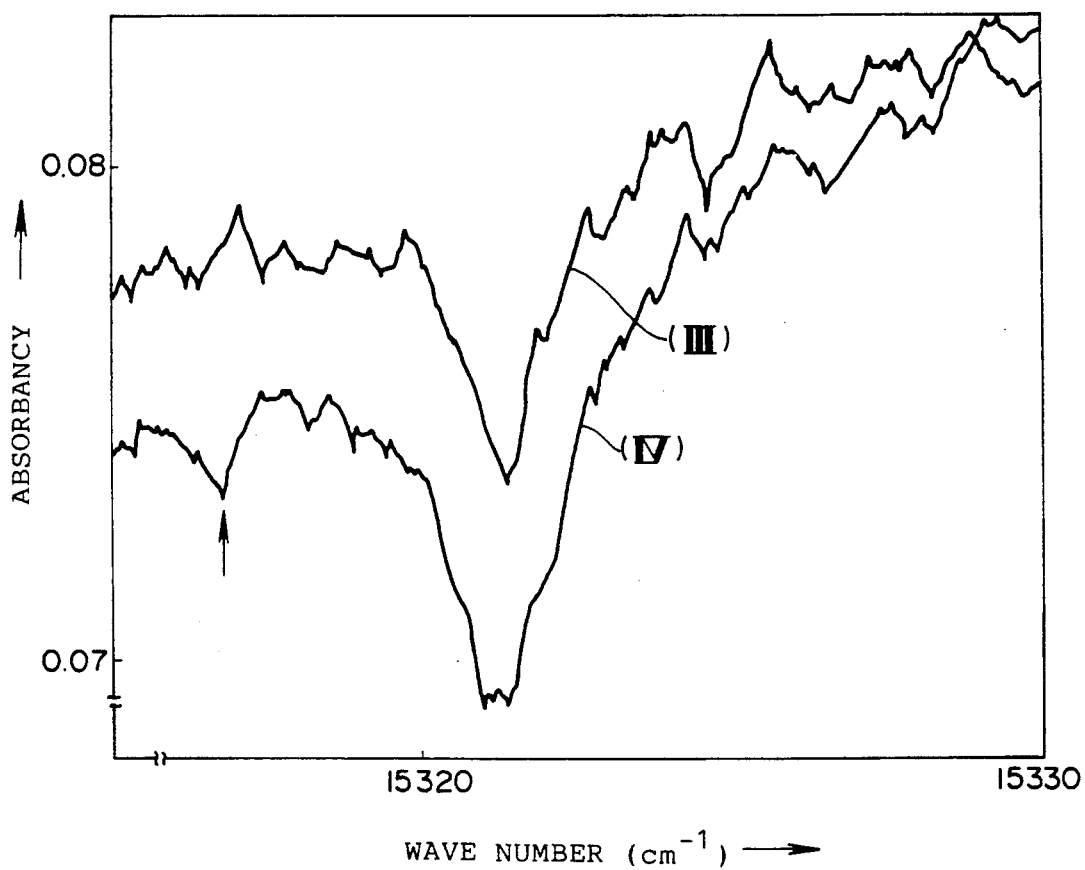
FIG. 3 shows a spectrum for a recording state obtained upon employing a wavelength multiplexed recording material containing tetraphenylporphine, as a comparative example.

As a comparative example, recording was performed using a recording material consisting of tetraphenyl porphine not having substituents in the benzene ring. The results are shown in FIG. 3, wherein the ordinate and the abscissa represent the absorbancy and the number of oscillation waves, respectively, and curves III and IV represent the spectra at the recording wavelengths of 5 and 8 percents, respectively. It is seen from this figure that the hole width becomes broader at the recording wavelength of 5 percent and even more broader at the recording wavelength of 8 percent. In the latter case, side holes appear at the site indicated by the arrow mark in the figure, this being an explicit element or factor in deteriorating the S/N ratio.

EXAMPLE 2

In the present Example, the wavelength multiplexed optical recording material including tetra(pentafluorophenyl) porphine as the photosensitive material as in the preceding Example was formed into a plate-shaped sample by a so-called polymer casting method, and wavelength multiplexed optical recording was made on this sample upon changing the oscillation wave numbers of the dye laser.

Polymethylmethacrylate with a molecular weight of $9-10^4$ was first dissolved in a suitable amount of acetone and tetra(pentafluorophenyl)porphine was added at a rate of $10^{-4}$/kg or in an amount of $10^{-2}$ wt. percent to polymethyl methacrylate. After the solvent acetone was volatized off, a plate about 1 mm thick was prepared. A small piece was cut as a sample from this plate and placed in a cryostat. A wavelength multiplexed writing test was conducted on this sample using a continuously oscillated dye laser excited by an argon ion laser as a light source. The wave number of the laser oscillation and the laser waveform were adjusted using a photon diode array such that the wave number of dye laser oscillation laser was changed in 114 ways at intervals of approximately 2.4 cm$^{-1}$ within the wavelength range of 15173.7 to 15446.0 cm$^{-1}$ or 6590 to 6476 Å . Each laser irradiation was continued for 30 seconds at an oscillation energy of 4.4 mW/cm$^2$.

Figure 4:
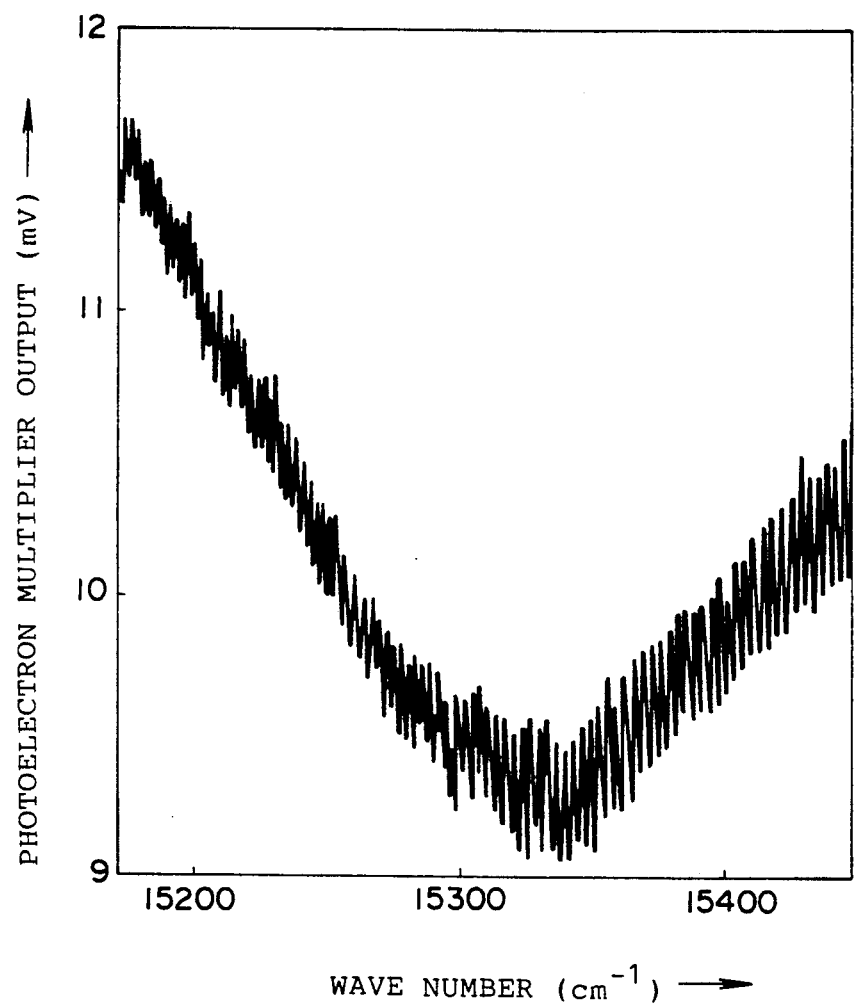
FIG. 4 shows an absorption spectrum for the wavelength multiplexed recording on a wavelength multiplexed recording material containing tetra(pentafluorophenyl)porphine as the photosensitive material.

The absorption spectrum of tetra(pentafluoro)porphine, obtained by the experiment, is shown in FIG. 4, wherein the ordinate represents the output in mV of a photoelectron multiplier tube and the abscissa the wave number in $cm^2$. It is apparent from this figure that 114 holes have been formed in each inhomogeneous absorption band in a one-to-one association with the respective laser wavelengths. It is also apparent that, since the side holes or anti-holes contributing to deterioration of the S/N ratio are not exhibited definitely, selection of the intensity of the interaction between the photosensitive material and the dispersion medium has been appropriately in the present system.

EXAMPLE 3

The wavelength multiplexed optical recording composition employed in the present Example is tetra(4-methoxyphenyl) porphine having a methoxy group as the electron donative substituent at the para-position of the benzene ring, and represented by the following structural formula IV:

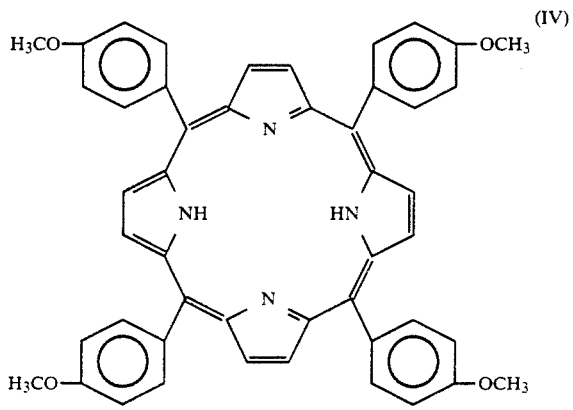

(IV)

Figure 5:
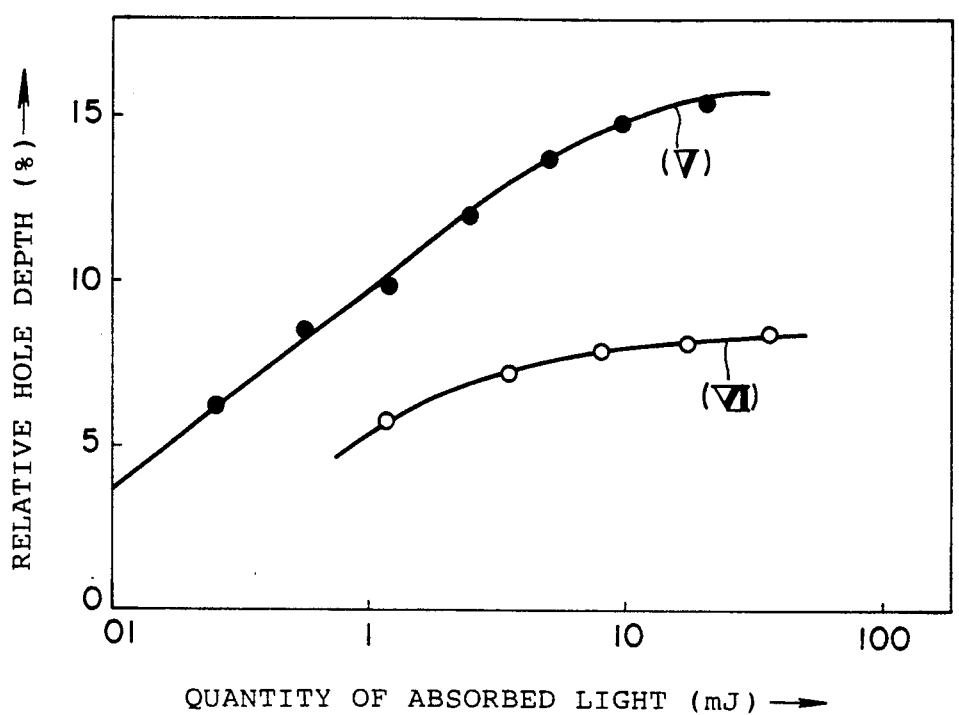
FIG. 5 is a characteristic diagram showing the absorbed light quantity dependency of the recording sensitivities of tetra(4-methoxyphenyl)porphine and tetraphenylporphine.

$1 \times 10^{-4}$ percent by weight of the above material was added to polymethylmethacrylate to form a sample. After the sample was cooled to 4K, recording was made thereon using a dye laser having an oscillation wave number of 15320.9 $cm^{-1}$ (wavelength, 6527Å) and an oscillation energy of 0.2 $mW/cm^2$. For comparison sake, similar tests were conducted on tetraphenylporphine not having substituents in the benzene ring. The results of comparison of these two tests are shown in FIG. 5 wherein the ordinate represents the relative hole depth and the abscissa the quantity of absorbed light in a log scale. The relative hole width herein means the rate of the decrease in absorbancy caused by hole formation to absorbancy prior to the occurrence of the photochemical hole burning, and may be used as a measure of the recording sensitivity. The black dots represent a sensitivity curve (V) for tetra(4-methoxyphenyl)porphine, while the white dots a sensitivity curve (VI) for tetraphenyl porphine. It is seen from this figure that the quantity of light absorption necessary to produce the relative hole depth of, for example, 6 percent, is 0.25 mJ for tetra(4methoxyphenyl)porphine, which is below the complete recording saturation within the range of observation of the present experiment, such that the recording sensitivity not less than 15 percent may be obtained in terms of the relative hole width. In the case of tetraphenylporphine, on the other hand, the quantity of light absorption necessary to induce the same relative hole depth of 6 percent is 1.5 mJ, and recording saturation occurs at the relative hole depth of about 10 percent. In the case of tetra(pentafluorophenyl) porphine in which fluorine atoms are introduced as the electron attractive substituent into the benzene ring, the quantity of light absorption necessary to induce the same relative hole depth of 6 percent is about 100 mJ, although the case is not shown specifically. Therefore, for the same relative hole depth of 6 percent, tetra(4-methoxyphenyl) porphine has the recording sensitivity about 6 times that of tetraphenylporphine and 400 times that of tetra(pentafluorophenyl)-porphine, while permitting recording with a higher S/N ratio, since recording saturation then occurs at a larger value of the relative hole depth.

EXAMPLE 4

In the present Example, the wavelength multiplexed optical recording material containing tetra(4-methoxyphenyl) porphine as the photosensitive material, as in the preceding Example 3, was formed into a plate-shaped sample, by relying upon the so-called polymer casting method, and the wavelength multiplexed recording was conducted on the sample, upon, changing the oscillation wavelengths of the dye laser.

Using tetra(4-methoxyphenyl)porphine, the plate-shaped sample was prepared in accordance with the method described in the preceding Example 3, and a wavelength multiplexed writing test was conducted using the same laser unit as in the preceding Example 3. The oscillation wave number of the dye laser was set to 15173.7 to 15446.0 $cm^{-1}$ (wavelength, 6590 to 6476 Å) and changed in 100 ways approximately at intervals of 3.3 $cm^{-1}$. Each laser irradiation was conducted for 10 seconds at a light intensity of 4.4 $mW/cm^2$.

Figure 6:
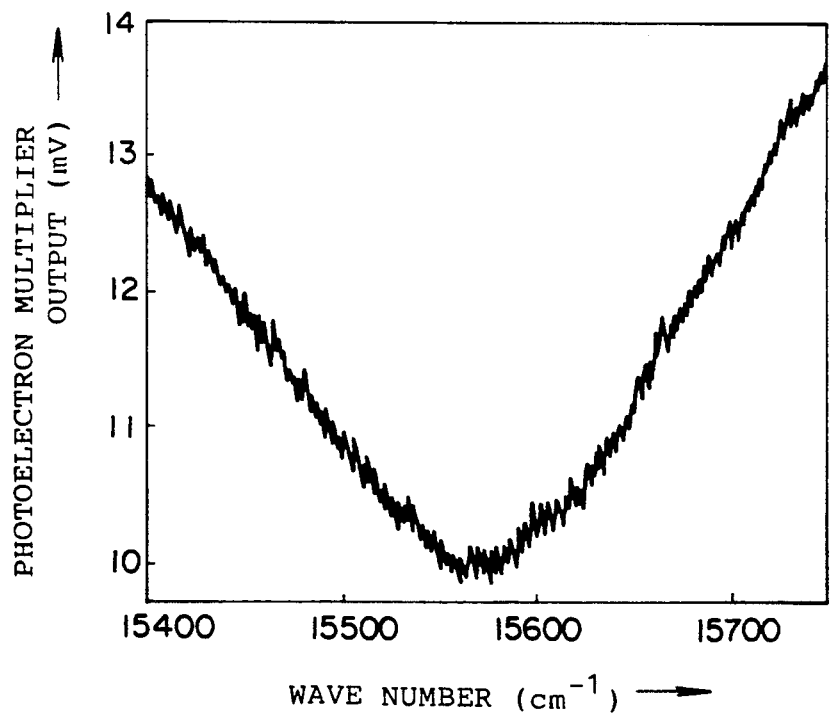
FIG. 6 is an absorption spectrum diagram for the wavelength multiplexed recording on a wavelength multiplexed recording material containing tetra(4-methoxyphenyl)porphine as the photosensitive material.

The absorption spectrum of tetra(4-methoxy)porphine, obtained with this test, is shown in FIG. 6, wherein the ordinate represents the output in mV of the photoelectron multiplier and the abscissa the wavelength in $cm^{-2}$. It is seen from this figure that 100 holes have been formed in the inhomogeneous absorption band in a one-to-one relative with the respective laser wave numbers. It is also seen that, since the side holes or anti-holes contributing to deterioration of the S/N ratio are not exhibited significantly, the intensity of the interaction between the photosensitive material and the dispersion medium has been selected appropriately in the present system.

What is claimed is:

1. The method of forming a recording member for use with a laser beam optical recording apparatus, comprising the steps of forming a recording layer consisting of material comprising:

a dispersing agent and a compound exhibiting persistent photochemical hole-burning having the following formula;

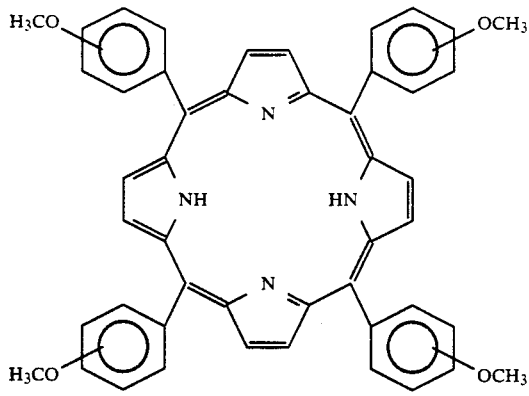
2. The method of forming a recording member for use with a laser beam optical recording apparatus, comprising the step of forming a recording layer consisting of material comprising:
a dispersing agent and a compound exhibiting persistent photochemical hole-burning having the following formula;
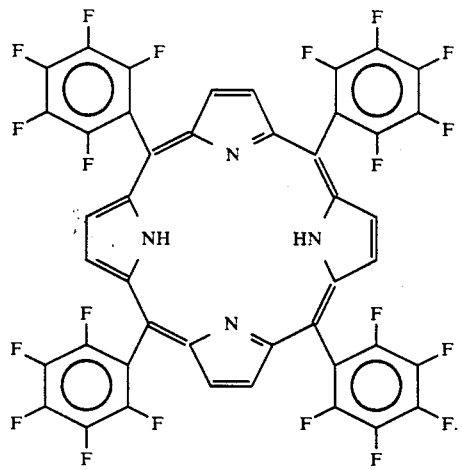
* * * * *